United States Patent
Waskönig et al.

[11] Patent Number: 5,364,373
[45] Date of Patent: Nov. 15, 1994

[54] EPIDURAL CANNULA

[75] Inventors: Wilhelm Waskönig, Aguadulce; José J. Rodiera Olive, Barcelona, both of Spain

[73] Assignee: te me na Logistics, Almeria, Spain

[21] Appl. No.: 50,074

[22] Filed: May 5, 1993

[30] Foreign Application Priority Data

Nov. 5, 1990 [ES] Spain .................. 9002795

[51] Int. Cl.$^5$ .................. A61M 5/32; A61M 5/00
[52] U.S. Cl. .................. 604/272; 604/117; 604/239
[58] Field of Search .................. 604/272–274, 604/264, 117, 239

[56] References Cited

U.S. PATENT DOCUMENTS

| | | | |
|---|---|---|---|
| 824,686 | 6/1906 | Daniel | 604/274 |
| 3,081,770 | 3/1963 | Hunter | 604/32 |
| 3,540,447 | 11/1970 | Howe | 604/165 |
| 4,002,174 | 1/1977 | Reed et al. | 604/272 X |
| 4,335,718 | 6/1982 | Calabrese | 604/272 X |
| 4,735,612 | 4/1988 | Chevalier | 604/272 X |
| 4,781,691 | 11/1988 | Gross | 604/264 X |
| 4,861,341 | 8/1989 | Woodburn | 604/272 X |
| 5,195,526 | 3/1993 | Michelson | 604/117 X |

Primary Examiner—John D. Yasko
Assistant Examiner—Frank Wilkens
Attorney, Agent, or Firm—Dennison, Meserole, Pollack & Scheiner

[57] ABSTRACT

An epidural cannula for local anesthesia having a cannula point with an adjacent lateral opening parallel to the longitudinal axis of the cannula. The cannula has a cross-sectional enlargement spaced from the point and having an area directed toward the point that forms an angle greater than 30° relative to the longitudinal axis of the cannula.

9 Claims, 2 Drawing Sheets

EPIDURAL CANNULA

BACKGROUND OF THE INVENTION

The invention relates to an epidural cannula for local anesthesia.

In epidural anesthesia, the point and the opening must be between the ligamenta flava and the dura mater. With conventional needles of constant diameter (see for example U.S. Pat. No. 2,922,420), the necessary force for injection is abruptly reduced at the moment the cannula point has penetrated the ligamenta flava, so that the risk of an unintended perforation of the dura mater increases. To prevent this, the physician using the epidural cannula must be skilled and experienced.

A cannula for use in operations is known from U.S. Pat. No. 3,081,770, of which the cannula body has a cross-sectional change at a distance from the cannula point. The area between the cross-sectional change and the cannula point having a central opening is rectangular or oval in cross-section.

The problem underlying the present invention is to provide an epidural cannula of the type mentioned at the outset such that it is largely ensured that an unintended perforation of the dura mater is prevented, i.e. it is ensured that the cannula point is inside the epidural area with its opening at a distance from this membrane for anesthesia or puncture.

SUMMARY OF THE INVENTION

The problem is solved in accordance with the invention by the measures set forth in the subordinate claims. These are characterized on the one hand in that the cannula body has a cross-sectional enlargement at a distance from the cannula point in the form of a bulge-like enlargement having at least one area towards the cannula point that describes an angle $\alpha$ in relation to the epidural cannula longitudinal axis, seen in the direction of the cannula point, with $\alpha > 30°$, and in that the distance between the proximal point of the microsection of the cannula and the end of the bulge-like enlargement away from the cannula point is approximately the thickness of the ligamenta flava. On the other hand, it is provided that the cannula body has at a distance from the cannula point a cross-sectional enlargement such that when a force is exerted on the epidural cannula in the direction of its point the forward motion of the cannula can be stopped when the enlargement enters the ligamenta flava, where the enlargement is formed at least in sections by a cannula body wall section at an angle $\alpha$ in relation to the longitudinal axis of the epidural cannula seen in the direction of the cannula point, with $\alpha > 30°$, and where the distance between the free front end of the cannula point and the start of the cross-sectional change of the epidural cannula body is identical to or smaller than the distance between the ligamenta flava and the dura mater at the lumbar level. Further embodiments are stated in the subclaims.

In accordance with the invention, preferably one abrupt change in cross-section, which must not necessarily be all round and/or symmetrical to the longitudinal axis of the cannula body, results in a buildup of a resistance against the movement when the enlargement contacts the ligamenta flava or is about to enter it. The force necessary to drive the needle further in also increases progressively with the penetration, such that no relaxation of force takes place when the ligamenta flava is penetrated—unlike with known epidural needles. Accordingly, a perforation of the dura mater is almost ruled out.

Even though cannulas are already known that have differing diameters along their longitudinal axes (see for example EP-A-0 359 987, U.S. Pat. Nos. 3,081,770, 3,540,447), these are not intended for solution of the problem underlying the invention, namely preventing perforation of the dura mater, but to reduce by their geometry complications arising from perforation of the dura mater. The cannulas mentioned are hence intended actually to perforate the dura mater while at the same time preventing the liquor leak syndrome to a large extent.

To ensure clear positioning of the lateral opening of the epidural needle between ligamenta flava and dura mater, the distance between the free front end of the cannula point and the start of the cross-sectional change of the epidural cannula body corresponds to the distance between ligamenta flava and dura mater at the lumbar level.

What is understood by distance here is not necessarily only the natural distance between ligamenta flava and dura mater, but also the distance which can apply when the cannula point comes up against the dura mater but without perforation of the latter, i.e. when the point contacts and stretches it. When the enlargement is designed in the shape of a bulge, its extension in the direction of the longitudinal axis of the epidural cannula should be equal to or less than the thickness of the ligamenta flava, such that the bulge can be completely inside the ligamenta flava when the cannula microsection is inside the epidural area. This ensures clear positioning of the cannula opening in the epidural area, so that uncontrolled pushing or pulling effects on the epidural cannula cannot lead to a change in position.

It is preferable for the difference between the diameters of the epidural cannula, the epidural area, so that uncontrolled pushing or pulling effects on the epidural cannula cannot lead to a change in position.

It is preferable for the difference between the diameters of the epidural cannula in front of the enlargement and of the enlargement itself to be a maximum of two gauges, preferably one gauge. The object in accordance with the invention is achieved by these changes in cross-section, namely that the stopping effect is made noticeable by the change in cross-section such that a risk of perforating the dura mater and the complications thereby involved are avoided during further penetration by the epidural cannula.

It can also be of advantage when the opening of the epidural cannula with its area towards the enlargement is at a distance from this area that is approximately equal to the thickness of the ligamenta flava.

Concerning the cannula point itself, it must be noted that it can have known microsections such as the Hustead or Tuohy types.

If the enlargement is not of the all round type, it should preferably extend peripherally over $\frac{2}{3}$ of the cannula body circumference.

Further details, advantages and features of the invention are given not only in the claims and in the features they describe—singly and/or in combination—but also in the following description of preferred embodiments as shown in the drawings.

DESCRIPTION OF PREFERRED EMBODIMENTS

Figure 1:
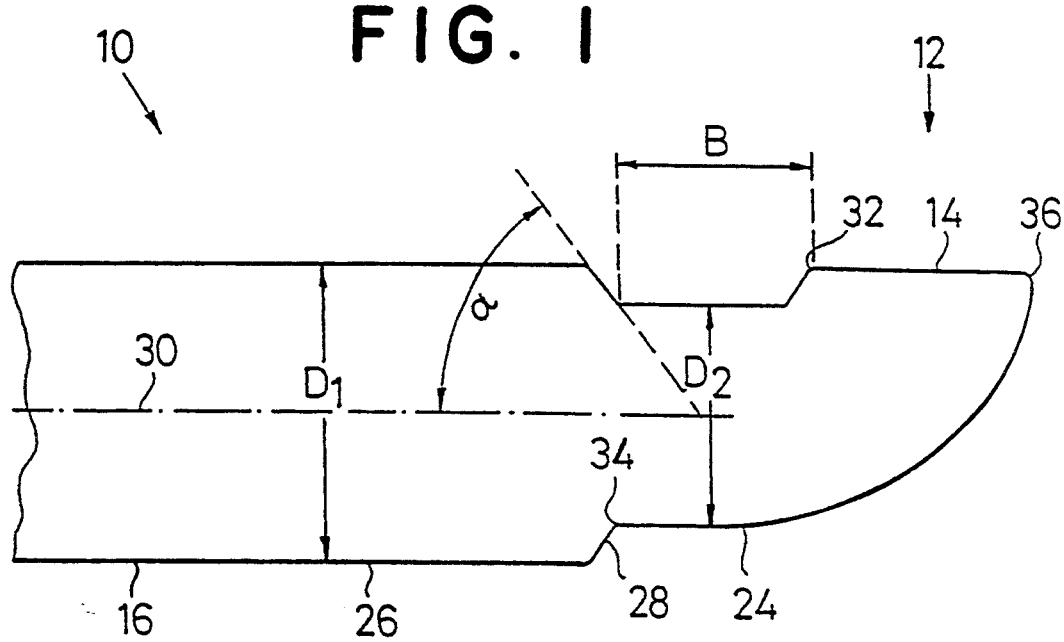
FIG. 1 shows a longitudinal section through a first embodiment of an epidural cannula.

FIG. 1 is a purely diagrammatic representation of an epidural cannula (10) having a cannula point (12) with lateral opening or microsection (14) and a cannula body (16) held by a holding means not shown in the drawing. To this extent it is a cannula of known type.

Figure 3:
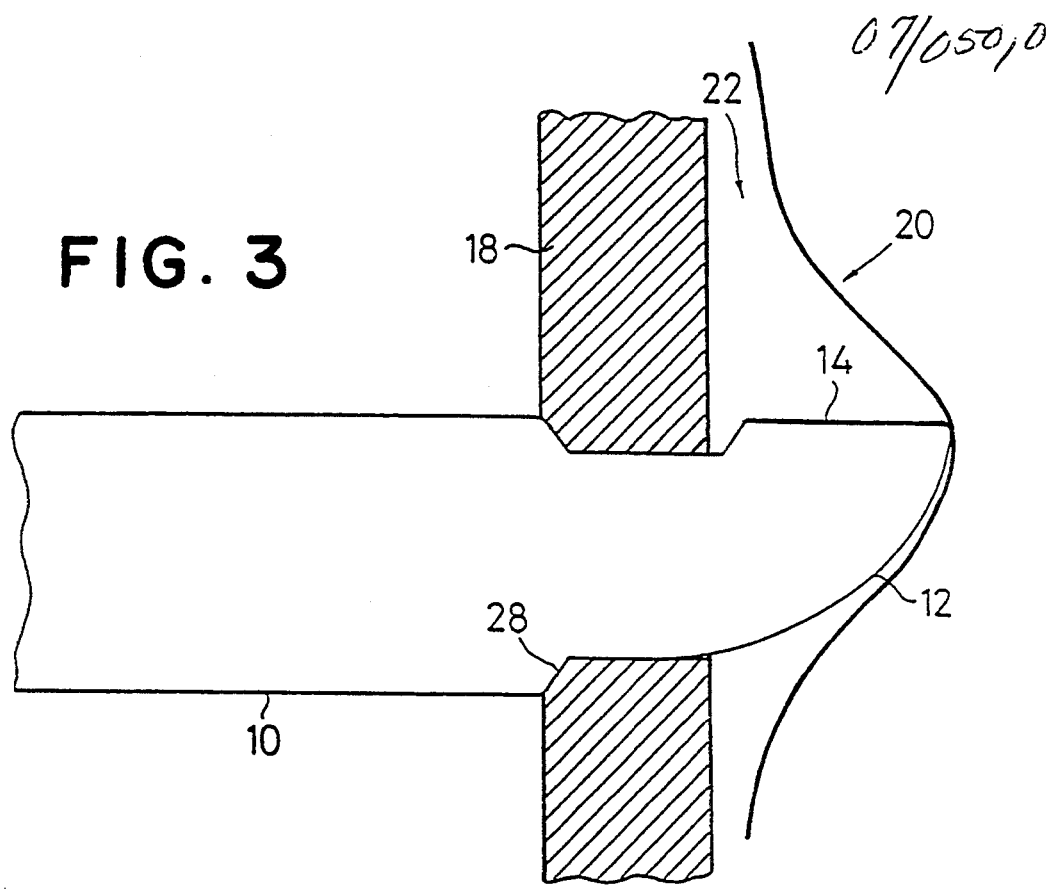
FIG. 3 shows the epidural cannula in accordance with FIG. 1 with a cannula opening disposed between ligamenta flava and dura mater.

It is now provided in accordance with the invention that the cross-section is changed between the cannula body (16) and the cannula point (12), leading to the epidural cannula (10) being stopped during penetration of the ligamenta flava (18) (FIG. 3). As a result, a substantially progressive change in the force is caused during further penetration of the ligamenta flava (18). This ensures that an uncontrolled penetration or perforation of a dura mater (20) is prevented, which could otherwise result in the known liquor leak syndrome.

In other words, the change in the cross-section is intended to ensure that the cannula point (12) with its opening (14) is clearly positionable in the epidural area (22) for anesthesia.

The change in the cross-section is shown in purely principle form by the differing diameters $D_2$ and $D_1$. The transition between the differing diameters, i.e. between the area (24) of the cannula point (12) with the diameter $D_2$ and the area (26) of the cannula body (16) with the diameter $D_1$, can be gradual here, but abrupt, as made clear in FIG. 1. This transition is numbered (28) and has a truncated-cone geometry.

The cannula body section, i.e. the transition (28) therefore describes in relation to the epidural cannula body longitudinal axis (30) an angle α that is preferably in the range from 30° to 60°, preferably 45°. This ensures an adequate stopping effect when the transition (28), i.e. the cross-sectional change, comes up against the ligamenta flava (18). This should take place when the microsection of diameter $D_1$, can be gradual here, but abrupt, as made clear in FIG. 1. This transition is numbered (28) and has a truncated-cone geometry.

The cannula body section, i.e. the transition (28) therefore describes in relation to the epidural cannula body longitudinal axis (30) an angle α that is preferably in the range from 30° to 60°, preferably 45°. This ensures an adequate stopping effect when the transition (28), i.e. the cross-sectional change, comes up against the ligamenta flava (18). This should take place when the microsection of the cannula point (12) has penetrated through the ligamenta flava (18). The distance B of the proximal point (32) of the needle microsection from the point (34) in which the cross-sectional change takes place should therefore be approximately the width of the ligamenta flava (18).

Figure 2:
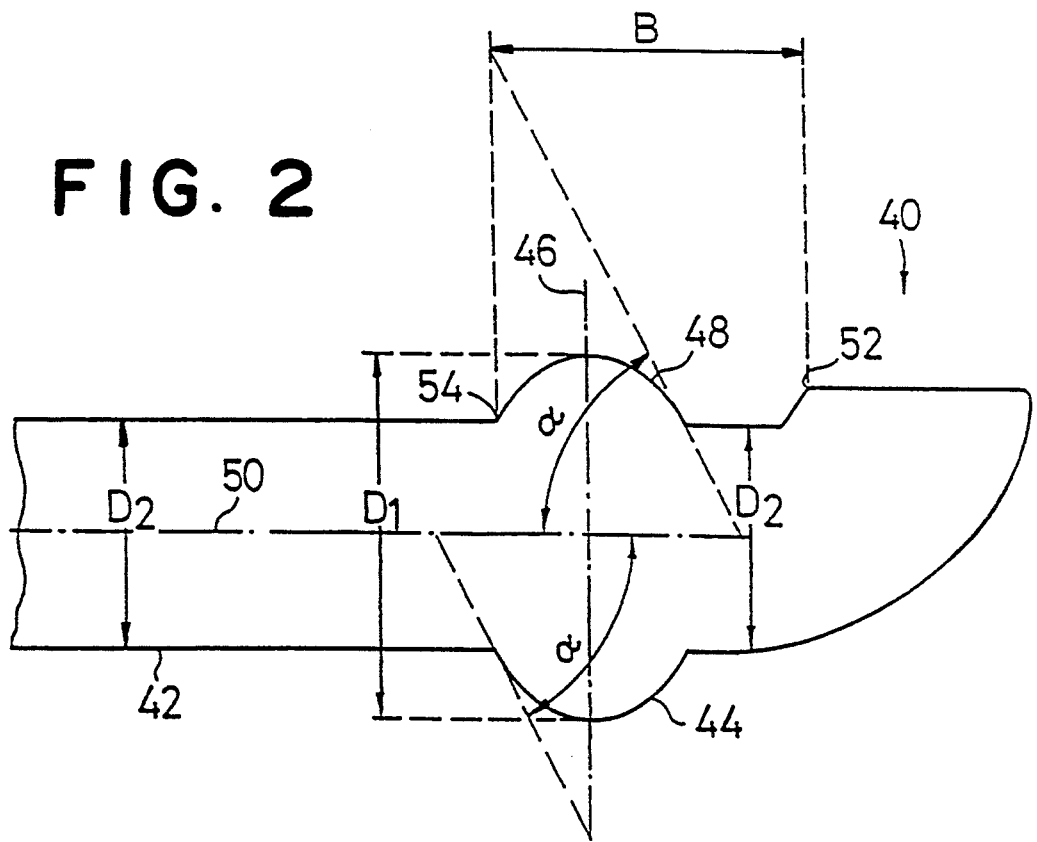
FIG. 2 shows a longitudinal section through a second embodiment of an epidural cannula.

FIG. 2 shows an epidural cannula (38) which also has a cannula point (40) and a cannula body (42), however where the diameter $D_2$ in the point area is also present in the area of the remaining cannula body (42), except for the all round enlargement (44), which may be described as a bulge and which causes a change in the cross-section that has the same function as the enlargement described in FIG. 1 (reference number 28).

The bulge-like widening (44) or bulge having a symmetrical pattern in relation to the cross-sectional plane (46) in the embodiment has in the section (48) towards the cannula point (40) at least in some areas an angle α in relation to the epidural cannula longitudinal axis (50) that is identical to that of the epidural cannula (10).

Figure 4:
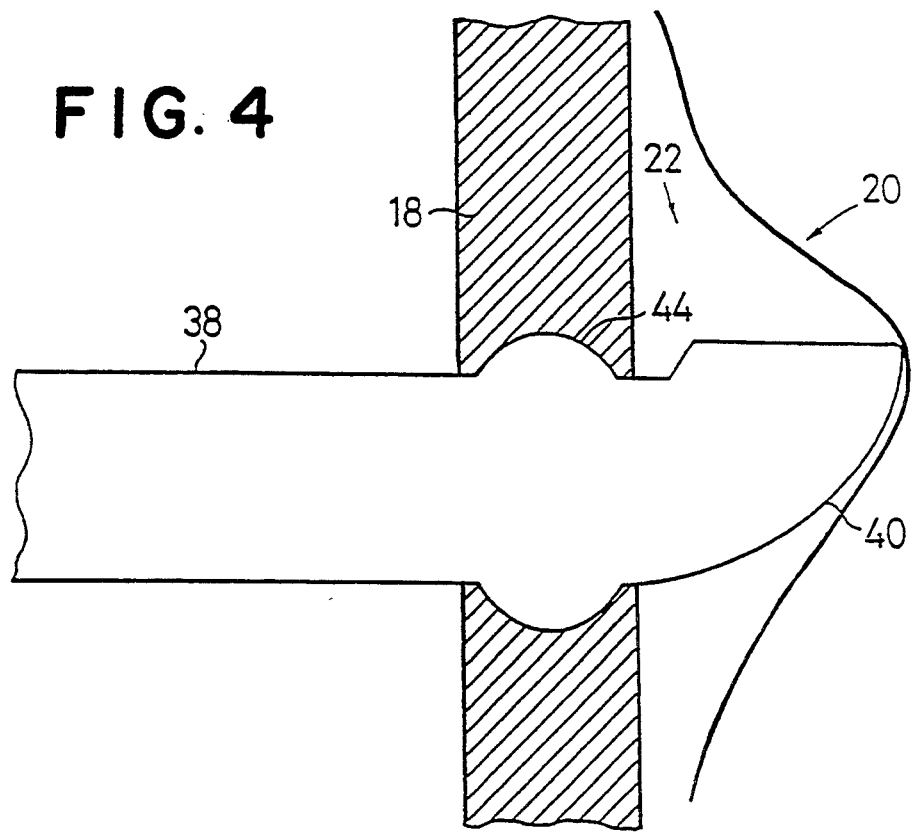
FIG. 4 shows the epidural cannula as shown in FIG. 2 with cannula opening disposed between ligamenta flava and dura mater.

The extension of the cross-sectional enlargement (44) in the longitudinal direction of the epidural cannula (38) should be selected such that there is, between the proximal point (52) of the microsection of the cannula point (40) and the end (54) away from the point (40), a distance B that is identical to the thickness of the ligamenta flava (18). This ensures that when the microsection of the cannula point (40) and hence the opening is inside the epidural area, the enlargement (44) is completely fixed in position in the ligamenta flava (18) so that uncontrolled pushing or pulling effects do not lead to a change in position of the epidural cannula (38), see FIG. 4.

The microsections of the epidural cannula (10) and (38) can be of conventional type, i.e. Hustead or Tuohy.

The following should be noted concerning the dimensions of the epidural cannulas (10) and (38) in accordance with the invention.

The distance between the proximal point (32) or (52) of the microsection and the start of the cross-sectional change (28) or (44) respectively should be in the order of magnitude of 2 mm.

With regard to the cross-sectional ratios—on the one hand in the area of the cannula point (12) or (40), on the other hand in the area of the enlargement (26) or (44)—a difference of at most 2 gauges, preferably 1 gauge should apply, with the diameter $D_2$ being preferably 19 or 18 gauges (1.00 mm or 1.20 mm) and the diameter $D_1$ 18 or 17 gauges (1.20 mm or 1.40 mm).

We claim:

1. An epidural cannula for anesthesia, comprising a cannula point having a microsection and with a lateral opening therein and a central, cylinder-shaped cannula body of which the end away from said point is connectable to that of a holding means, said point lateral opening being in a plane parallel to the longitudinal axis of said cannula, where said lateral opening of said cannula is positionable during the use of said epidural cannula between the ligamenta flava and the dura mater, wherein said cannula body has a cross-sectional enlargement at a distance from said cannula point and in the form of a bulge-like enlargement having at least one area toward said cannula point that describes an angle α with α>30° in relation to said epidural cannula longitudinal axis, seen in the direction of said cannula point, and wherein the distance (B) between the proximal point of said cannula microsection and the end of said bulge-like enlargement away from said cannula point is approximately as thick as said ligamenta flava.

2. An epidural cannula according to claim 1, wherein said bulge-like enlargement is designed symmetrically in relation to a cross-sectional plane.

3. An epidural cannula according to claim 1 or 2, wherein said epidural cannula has a diameter in the area of its point of 17 gauges, and said enlargement a maximum diameter of 18 gauges.

4. An epidural cannula according to claim 1 or 2, wherein the distance between the free front end of said cannula point and the start of said enlargement is identical to or smaller than the distance between said ligamenta flava and said dura mater at the lumbar level.

5. An epidural cannula for anesthesia, comprising a cannula point with a lateral opening and microsection, and a central, cylinder-shaped cannula body of which the end away from said cannula point is connectable to a holding means, where said lateral opening of said point of said epidural cannula is in a plane generally parallel to the longitudinal axis of said cannula body and is positionable during the use of said epidural cannula between the ligamenta flava and the dura mater, wherein said cannula body has a cross-sectional enlargement at a distance from said cannula point such that when a force is exerted on said epidural cannula in the direction of its point the forward motion of said cannula can be stopped when said enlargement enters said ligamenta flava, where said enlargement is formed at least in sections by a cannula body wall section at an angle a in relation to said longitudinal axis of said epidural cannula, seen in the direction of said cannula point, with $\alpha > 30°$, and where the distance between the free front end of said cannula point and the start of said enlargement is identical to or smaller than the distance between said ligamenta flava and said dura mater at the lumbar level.

6. An epidural cannula according to claim 5, wherein the difference between the diameter of said epidural cannula in front of said enlargement thereof and that of said enlargement is a maximum of 0.4 mm.

7. An epidural cannula according to claim 5, wherein said enlargement is of all-round design where it peripherally extends over two thirds of the circumference of said cannula body.

8. An epidural cannula according to claim 1 or 5, wherein said cannula point has a Hustead microsection.

9. An epidural cannula according to claim 1 or 5, wherein said cannula point has a Tuohy microsection.

* * * * *